United States Patent
Soller et al.

(10) Patent No.: US 9,057,689 B2
(45) Date of Patent: Jun. 16, 2015

(54) METHODS AND SYSTEMS FOR ANALYTE MEASUREMENT

(75) Inventors: Babs R. Soller, Northboro, MA (US); Fengmei Zou, Shrewsbury, MA (US); Ye Yang, Westbrook, ME (US); Randy Ross, Northboro, MA (US); Boyan Peshlov, Chesterfield, MO (US)

(73) Assignees: University of Massachusetts, Boston, MA (US); Reflectance Medical, Inc., Westboro, MA (US)

(*) Notice: Subject to any disclaimer, the term of this patent is extended or adjusted under 35 U.S.C. 154(b) by 1011 days.

(21) Appl. No.: 13/011,113

(22) Filed: Jan. 21, 2011

(65) Prior Publication Data

US 2011/0184683 A1    Jul. 28, 2011

Related U.S. Application Data (60) Provisional application No. 61/297,664, filed on Jan. 22, 2010.

(51) Int. Cl.
*G01D 18/00* (2006.01)
*G01N 21/3577* (2014.01)
*G01N 33/49* (2006.01)

(52) U.S. Cl.
CPC ........ *G01N 21/3577* (2013.01); *G01N 33/4925* (2013.01)

(58) Field of Classification Search
CPC ................ G01N 21/3577; G01N 33/4925
USPC .......................................................... 702/85
See application file for complete search history.

(56) References Cited

U.S. PATENT DOCUMENTS

| | | | |
|---|---|---|---|
| 5,582,170 A | 12/1996 | Soller | |
| 5,813,403 A | 9/1998 | Soller et al. | |
| 6,006,119 A | 12/1999 | Soller et al. | |
| 6,304,767 B1 | 10/2001 | Soller et al. | |
| 6,564,088 B1 | 5/2003 | Soller et al. | |
| 6,766,188 B2 | 7/2004 | Soller | |
| 7,245,373 B2 | 7/2007 | Soller et al. | |
| 7,460,895 B2 * | 12/2008 | Arnold et al. | 600/310 |
| 7,532,919 B2 | 5/2009 | Soyemi et al. | |
| 7,616,303 B2 | 11/2009 | Yang et al. | |
| 7,881,892 B2 | 2/2011 | Soyemi et al. | |

(Continued)

FOREIGN PATENT DOCUMENTS

| WO | WO 2008/116835 | 10/2008 |
|---|---|---|
| WO | WO 2010/053617 | 5/2010 |

OTHER PUBLICATIONS

Alam et al., "Measurement of pH in whole blood by near-infrared spectroscopy," Appl. Spectroscopy 53: 316-324 (1999).

(Continued)

*Primary Examiner* — Tung S Lau
*Assistant Examiner* — Xiuquin Sun
(74) *Attorney, Agent, or Firm* — Fish & Richardson P.C.

(57) ABSTRACT

Methods are disclosed for determining a value associated with an analyte in a sample. The methods include: determining a set of spectra from a model for light attenuation in the sample, where the model includes contributions from at least two different sources of light attenuation in the sample; determining a set of spectral correction factors associated with the analyte in the sample based on the set of spectra; and using the set of spectral correction factors to determine the value associated with the analyte of interest.

16 Claims, 5 Drawing Sheets

(56) References Cited

U.S. PATENT DOCUMENTS

| | | | |
|---|---|---|---|
| 2003/0032064 A1 | 2/2003 | Soller et al. | |
| 2004/0005717 A1 | 1/2004 | Soller | |
| 2004/0204868 A1 | 10/2004 | Maynard et al. | |
| 2008/0097173 A1* | 4/2008 | Soyemi et al. | 600/310 |
| 2009/0024013 A1 | 1/2009 | Soller | |

OTHER PUBLICATIONS

Arridge et al., "The theoretical bases for the determination of optical pathlengths in tissue: temporal and frequency analysis," Phys. Med. Biol. 37(7): 1531-1560 (1992).

Bland et al., "Statistical methods for assessing agreement between two methods of clinical measurement," The Lancet 327: 307-310 (1986).

Brazy et al., "Noninvasive monitoring of cerebral oxygenation in preterm infants: preliminary observation," Pediatrics 75: 217-225 (1985).

Cubeddu et al., "A solid tissue phantom for photon migration studies", Phys. Med. Biol. 42: 1971-1979 (1997).

Cui et al., "Experimental study of migration depth for the photons measured at sample surface. I. Time resolved spectroscopy and imaging," Proc. SPIE 1431: 180-191 (1991).

Doornbos et al., "The determination of in vivo human tissue optical properties and absolute chromophores concentrations using spatially resolved steady-state diffuse reflectance spectroscopy," Phys. Med. Biol. 44: 967-981 (1999).

Farrell et al., "A diffusion theory model of spatially resolved, steady-state diffuse reflectance for the noninvasive determination of tissue optical properties in vivo," Med. Phys. 19(4): 879-888 (1992).

Franceschini et al., "Near-infrared spiroximetry: noninvasive measurements of venous saturation in piglets and human subjects," J. Appl. Physiol. 92: 372-384 (2002).

Glaister et al., "A near-infrared spectrophotometric method for studying brain $O_2$ sufficiency in man during +Gz acceleration," Aviat. Space Environ. Med. 59: 199-207 (1988).

Haaland et al., "Partial least-squares methods for spectral analyses. 1. Relation to other quantitative calibration methods and the extraction of qualitative information," Anal. Chem. 60: 1193-1202 (1988).

Hirsch et al., "Near-infrared spectroscopy: What we know and what we need to know—A systematic review of the congenital heart disease literature," J. Thorac. Cardiovasc. Surg. 137: 154-159 (2009).

International Search Report and Written Opinion in PCT Application No. PCT/US2011/022095, dated Jul. 26, 2011.

Kelman, "Digital computer subroutine for the conversion of oxygen tension into saturation," J. Appl. Physiol. 21: 1375-1376 (1966).

Kienle et al., "Improved solutions of the steady-state and the time-resolved diffusion equations for reflectance from a semi-infinite turbid medium," J. Opt. Soc. Am. A 14: 246-254 (1997).

Kienle et al., "Noninvasive determination of the optical properties of two-layered turbid media," Appl. Optics 37(4): 779-791 (1998).

Liemert et al., "Light diffusion in N-layered turbid media: steady-state domain," J. Biomed. Optics 15(2): 025003-1-025003-10 (2010).

Liu et al., "Influence of blood vessels on the measurement of hemoglobin oxygenation as determined by time-resolved reflectance spectroscopy," Med. Phys. 22(8): 1209-1217 (1995).

Matcher et al., "Use of the water absorption spectrum to quantify tissue chromophore concentration changes in near-infrared spectroscopy," Phys. Med. Biol. 38: 177-196 (1993).

Neary, "Application of near infrared spectroscopy to exercise sports science," Can. J. Appl. Physiol. 29(4): 488-503 (2004).

Onozawa et al., "A new evaluation method for +Gz tolerance with loratadine by using a near-infrared spectroscopy," Dynamic Medicine 7:3 (2008).

Pereira et al., "A brief review of the use of near infrared spectroscopy with particular interest in resistance exercise," Sports Medicine 37(7): 615-624 (2007).

Quaresima et al., "The use of near infrared spectroscopy in sports medicine," J. Sports Med. Phys. Fitness 43(1): 1-13 (2003).

Roggan et al., "Optical Properties of Circulating Human Blood in the Wavelength Range 400-2500 nm," J. Biomed. Optics 4(1): 36-46 (1999).

Rovati et al., "Design and performance of a wide-bandwidth and sensitive instrument for near-infrared spectroscopic measurements on human tissue," Rev. Sci. Instrum. 75(12): 5315-5325 (2004).

Severinghaus, "Simple, accurate equations for human blood O2 dissociation computations," J. Appl. Physiol.: Respirat. Environ. Exercise Physiol. 46: 599-602 (1979).

Simonson et al., "Near-Infrared Spectroscopy: Clinical Applications," Critical Care Clinics, 12(4): 1019-1029 (1996).

Soller et al., "Feasibility of non-invasive measurement of tissue pH using near-infrared reflectance spectroscopy," J. Clin. Monit. 12: 387-395 (1996).

Soller et al., "Noninvasive, NIRS-measured muscle pH and PO2 indicate tissue perfusion for cardiac surgical patients on cardiopulmonary bypass," Crit. Care Med. 31: 2324-2331 (2003).

Soyemi et al., "Skin color correction for tissue spectroscopy: demonstration of a novel approach with tissue-mimicking phantoms," Appl. Spectroscopy 59(2): 237-244 (2005).

Van Staveren et al., "Light Scattering in Intralipid-10% in the wavelength range of 400-1100nm," Applied Optics 30: 4507-4514 (1991).

Ward et al., "Near infrared spectroscopy for evaluation of the trauma patient: a technology review," Resuscitation 68(1): 27-44 (2006).

Wyatt et al., "Quantification of cerebral oxygenation and haemodynamics in sick newborn infants by near infrared spectrophotometry," Lancet 2: 1063-66 (1986).

Yang et al., "Noninvasive in vivo Measurement of Venous Blood pH during Exercise using NIR Reflectance Spectroscopy," Appl. Spectrosc. 61: 223-229 (2007).

Yang et al., "Quantitative measurement of muscle oxygen saturation without influence from skin and fat using continuous-wave near infrared spectroscopy," Opt. Exp. 15: 13715-13730 (2007).

Yang et al., "Removal of Analyte-Irrelevant Variations in Near-Infrared Tissue Spectra," Appl. Spectroscopy 60(9): 1070-1077 (2006).

Yang et al., "Simultaneous correction of skin color and fat thickness for tissue spectroscopy using a two-distance fiber optic probe and orthogonalization technique," Opt. Lett. 30: 2269-2271 (2005).

Zhang et al., "Investigation of Noninvasive in Vivo Blood Hematocrit Measurement Using NIR Reflectance Spectroscopy and Partial Least-Squares Regression," Appl. Spectroscopy 54(2): 294-299 (2000).

Zhang et al., "Partial least-squares modeling of near-infrared reflectance data for noninvasive in-vivo determination of deep-tissue pH," Appl. Spectroscopy 52: 400-406 (1998).

Zou et al., "Feasibility of analyte prediction in phantoms using a theoretical model of near-infrared spectra," Proc. of SPIE vol. 7572, 757201-1-757201-9 (2010).

* cited by examiner

METHODS AND SYSTEMS FOR ANALYTE MEASUREMENT

CROSS-REFERENCE TO RELATED APPLICATIONS

This application claims priority to U.S. Provisional Patent Application No. 61/297,664 entitled "METHODS AND SYSTEMS FOR ANALYTE MEASUREMENT", filed on Jan. 22, 2010, the entire contents of which are incorporated herein by reference.

STATEMENT AS TO FEDERALLY SPONSORED RESEARCH

This invention was made with Government support under National Space Biomedical Research Institute grant no. SMS01301. The Government has certain rights in this invention.

TECHNICAL FIELD

This disclosure relates to measurement of analytes in biological samples.

BACKGROUND

Properties of biological samples can be measured by measuring light emitted from such samples following illumination. Incident illumination light is attenuated by samples and the nature of the illumination can provide information about sample constituents. In heterogeneous sample environments, the mechanism of light attenuation can be relatively complex.

SUMMARY

Disclosed herein are methods and systems for generating sets of spectral data that can be used to construct calibration equations for determinations of quantities associated with analytes of interest in biological samples. Mathematical generation (e.g., simulation) of spectral data that can be used to estimate spectral data that would otherwise be measured from samples can be considerably more efficient than collecting similar data from human or animal subjects. Moreover, when the spectral data is mathematically generated, the range of parameters that control the light attenuation properties of samples can be systematically varied, yielding spectral databases in which each of the relevant parameters spans a desired range of values. Thus, the database can encompass sample spectral information that is influenced by multiple sample properties.

The database spectra can be used to generate calibration equations for analytes of interest by suitably selecting particular members of the database that are used, for example, in a partial least squares regression analysis to determine equation parameters. The database spectra can also be matched to measured spectral information for a particular sample, and the closest matching database spectrum—rather than the measured spectral information—can be used as input into a corresponding calibration equation to determine the value associated with the analyte of interest in a sample. In this manner, the measured spectral information plays no direct role in the determination of analyte values, except in the identification of a closest member of the spectral database. Instead, determination of analyte values proceeds primarily on the basis of spectra that are generated mathematically from a model, avoiding sources of variability that are normally associated with data obtained from biological samples, and further significantly reducing the number of measurements that are made from human subjects. Sample analyte values can therefore be determined rapidly and accurately. Exemplary analytes for which values can be determined include pH, temperature, oxygen tension, oxygen saturation, carbon dioxide partial pressure, hemoglobin concentration, water concentration, and hematocrit.

In general, in a first aspect, the disclosure features methods for determining a value associated with an analyte in a sample, the methods including: determining a set of spectra from a model for light attenuation in the sample, where the model includes contributions from at least two different sources of light attenuation in the sample; determining a set of spectral correction factors associated with the analyte in the sample based on the set of spectra; and using the set of spectral correction factors to determine the value associated with the analyte.

Embodiments of the methods can include any one or more of the following features.

The at least two different sources of light attenuation can include light scattering and absorption. The light scattering can include contributions from light scattering by one or more fat layers and light scattering by muscle tissue. The absorption can include contributions from light absorption by at least two different analytes. The analyte can include at least one member selected from the group consisting of pH, temperature, oxygen tension, oxygen saturation, carbon dioxide partial pressure, hemoglobin concentration, water concentration, and hematocrit. The at least two different analytes can include oxygenated hemoglobin, de-oxygenated hemoglobin, and myoglobin.

Determining the set of spectral correction factors can include determining mean-centered spectra from the set of spectra. Determining the set of spectral correction factors can include determining orthogonalized spectra based on the mean-centered spectra.

Determining the value associated with the analyte can include using the set of spectral correction factors to correct at least one member of the set of spectra, and using the corrected at least one member of the set of spectra as input to a calibration equation for the analyte. Determining the value associated with the analyte can include obtaining measured spectral information for the sample, and determining a member of the set of spectra that is closest to the measured spectral information. The method can include determining the member of the set of spectra that is closest to the measured spectral information based on maximum and minimum differences between the measured spectral information and at least some of the members of the set of spectra. Determining the value associated with the analyte can include using the member of the set of spectra that is closest to the measured spectral information as input to the calibration equation, and determining the value associated with the analyte from the calibration equation.

The calibration equation can be derived from a partial least squares regression analysis of the set of spectra. Alternatively, or in addition, the calibration equation can correspond to a Taylor series expansion that relates spectral information to values of the analyte.

The method can include determining the value associated with the analyte based on a subset of members of the set of spectra that correspond to a common value of the analyte.

Determining the value associated with the analyte can include simulating spectral information for the sample using the model for light attenuation in the sample, using the simulated spectral information as input to the calibration equation, and determining the value associated with the analyte from the calibration equation.

Embodiments of the methods can also include any of the other features or steps disclosed herein, as appropriate.

In another aspect, the disclosure features methods for determining a value associated with an analyte in a sample, the methods including: determining a set of spectra from a model for light attenuation in a sample; obtaining spectral information corresponding to the sample and identifying a member of the set of spectra that corresponds to the spectral information; and determining the value associated with the analyte in the sample based on the identified member of the set of spectra.

Embodiments of the methods can include one or more of the following features.

The model for light attenuation can include contributions from light scattering and absorption by the sample. The light scattering can include contributions from light scattering by one or more fat layers and light scattering by muscle tissue. The absorption can include contributions from light absorption by at least two different analytes.

Identifying a member of the set of spectra can include determining maximum and minimum differences between the spectral information and at least some members of the set of spectra, and identifying the member of the set of spectra that corresponds to the spectral information based on the maximum and minimum differences.

Determining the value associated with the analyte can include using the identified member of the set of spectra as input to one or more a calibration equations that relate spectral information to values of the analyte. Determining the value associated with the analyte can include determining spectral correction factors associated with the analyte from the set of spectra, applying the spectral correction factors to the identified member of the set of spectra to correct the identified member, and using the corrected identified member as input to the calibration equation.

The methods can include determining the value associated with the analyte based on a subset of members of the set of spectra that correspond to a common value of the analyte.

The one or more calibration equations that relate spectral information to values of the analyte can be derived from a partial least squares regression analysis of the set of spectra. Alternatively, or in addition, the calibration equation can correspond to a Taylor series expansion that relates spectral information to values of the analyte.

The analyte can include at least one member selected from the group consisting of pH, temperature, oxygen tension, oxygen saturation, carbon dioxide partial pressure, hemoglobin concentration, water concentration, and hematocrit. The at least two different analytes can include oxygenated hemoglobin, de-oxygenated hemoglobin, and myoglobin.

Obtaining spectral information corresponding to the sample can include determining the spectral information from the model for light attenuation, and determining the value associated with the analyte can include using the identified member of the set of spectra as input to a calibration equation that relates spectral information to values of the analyte.

Embodiments of the methods can also include any of the other features or steps disclosed herein, as appropriate.

In a further aspect, the disclosure features systems for determining a value associated with an analyte in a sample, the systems including a radiation source configured to direct radiation to be incident on the sample, a detector configured to detect radiation from the sample, and an electronic processor configured or programmed to: (a) obtain measured spectral information about the sample based on the detected radiation; (b) compare the measured spectral information to a set of spectra determined from a model for light attenuation in the sample to identify a member of the set of spectra that corresponds to the measured spectral information; (c) correct the identified member of the set of spectra using a set of spectral correction factors determined from the set of spectra; and (d) use the corrected identified member of the set of spectra as input to a calibration equation to determine the value associated with the analyte.

Embodiments of the systems can include one or more of the following features.

The calibration equation can be stored in a memory unit connected to the electronic processor. The electronic processor can be configured to determine values associated with two or more analytes, where the two or more analytes are selected from the group consisting of pH, temperature, oxygen tension, oxygen saturation, carbon dioxide partial pressure, hemoglobin concentration, water concentration, and hematocrit.

Embodiments of the systems can also include any of the other features disclosed herein, as appropriate. Further, embodiments of the systems can perform any of the methods and/or method steps disclosed herein, as appropriate. The electronic processor can be configured to perform any of the methods or method steps.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Near infrared light can be used to illuminate biological samples, and light collected from such samples (e.g., illumination light that has been transmitted through samples and/or reflected from samples) can be used to obtain information about the samples. More particularly, near infrared light passes through skin and subcutaneous fat layers, and illuminates underlying muscle tissues. Some of the light can be absorbed by hemoglobin in red blood cells in the tissues, by water, and by proteins in blood plasma. Portions of the illumination light can also be scattered by muscle fibers and blood cells. Light collected from a sample illuminated in this manner can be detected as spectral information about the sample; that is, the detected light can be spectrally resolved in a suitable detector to measure the intensity of the collected light as a function of wavelength. The spectral information can be further analyzed to obtain information about one or more analytes of interest (e.g., light-absorbing components) in the sample, through a model for the sample's absorption spectrum that quantifies contributions of sample components to the sample's light absorption spectrum. Systems and methods for obtaining information about sample properties such as tissue pH, hematocrit, oxygen tension, and tissue oxygen saturation have been disclosed in the following U.S. Patents, the entire contents of each of which are incorporated herein by reference: U.S. Pat. No. 5,813,403; U.S. Pat. No. 6,006,119; U.S. Pat. No. 6,304,767; U.S. Pat. No. 6,766,188; and U.S. Pat. No. 7,532,919.

The general methodology employed in determining values associated with one or more sample properties typically includes measuring a large quantity of reference spectral information from a relatively large group of human subjects to develop a spectral library of information that spans different ranges associated with different sample parameters (e.g., muscle scattering coefficient, muscle absorption coefficient, pH, temperature). Subject-to-subject variability in muscle tissue light scattering can be reduced and/or removed to enable more accurate measurements to be made on human subjects. Systems and methods for reducing such variability are disclosed, for example, in U.S. Pat. No. 7,616,303, the entire contents of which are incorporated herein by reference.

Typically, calibration equations that are used to calculate the values associated with sample properties from measured spectral information are developed using statistical techniques that relate the reference spectral information discussed above to standard measurements of the values obtained through other means. To employ these methods, the analytes of interest in the reference spectral information span a relatively large range of values; in some embodiments, the range includes essentially the entire physiological ranges associated with the analytes. To measure the reference spectral information, human subjects are selected and experimental conditions manipulated so that the reference spectral information represents a wide range of such values. The accuracy of the obtained calibration equations can also be improved if other parameters that affect the sample's absorption spectrum, such as oxygen concentration, carbon dioxide concentration, temperature, and tissue scattering properties can be varied in a controlled manner.

A very large amount of data can be collected when a number of different analytes are to be analyzed. Further, in some embodiments, correlations occur between spectral effects produced by different analytes in a sample. These correlations can be difficult to separate into separate contributions from each of the analytes. As a result, the correlations can be implicitly reflected in calibration equations derived from the reference data; such equations may work well on some patients, but less well on others.

As an example, to account for subject-to-subject variation in muscle light scattering properties, principal component analysis (PCA) loading correction methods can be used to reduce the variations. To derive PCA correction factors for a calibration equation for a particular analyte or sample property, reference spectra from a large number of human subjects corresponding to a single value of the analyte or parameter in the subjects are analyzed to determine the PCA correction factors. It can be time consuming and expensive to obtain a large enough set of reference spectral information for accurate determination of PCA correction factors by performing measurements on a large number of human patients.

The present disclosure provides methods and systems for calculating reference spectral information in the form of sets of simulated spectra that correspond to different values of analytes and sample properties; the different values of the analytes and sample properties essentially correspond to making measurements from a wide variety of different samples under different conditions. By calculating rather than directly measuring the spectral information, the time and expense associated with developing a large spectral database of reference information can be significantly reduced. The reference spectral information can be partly or fully calculated each time an analyte value is measured. Alternatively, or in addition, some or all of the calculated reference spectral information can be stored in a memory unit and retrieved as need to obtain analyte measurements from samples. For example, the calculated reference spectral information can be used to determine correction factors (e.g., PCA correction factors) that are used to correct the reference spectral information for variations that do not correspond to sample analytes of interest.

Further, the corrected set of reference spectra can be used in statistics-based modeling methods such as partial least squares (PLS) regression analysis to develop calibration equations for sample analytes of interest. The calibration equations can be used with either measured sample spectral information or calculated spectral information from the reference information database to determine values associated with the analyte(s) of interest in particular samples.

This disclosure is divided into multiple parts. In the first part, general systems for measuring light from biological samples and determining sample properties based on the measured light are disclosed. In the second part, the general methodology employed to calculate reference spectra, obtain calibration equations, and determine values related to sample analytes is disclosed. In the third part of the disclosure, examples of the use of the methods and systems disclosed herein are discussed.

Measurement Systems

Figure 1A:
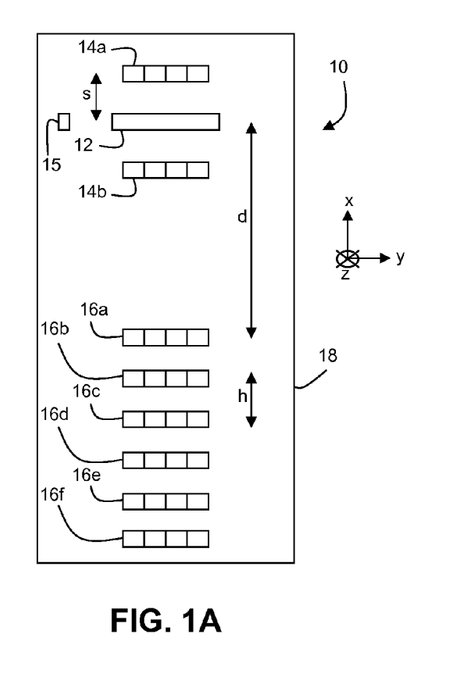
FIGS. 1A and 1B are bottom and top schematic diagrams, respectively, of an embodiment of a sensor.
Figure 1B:
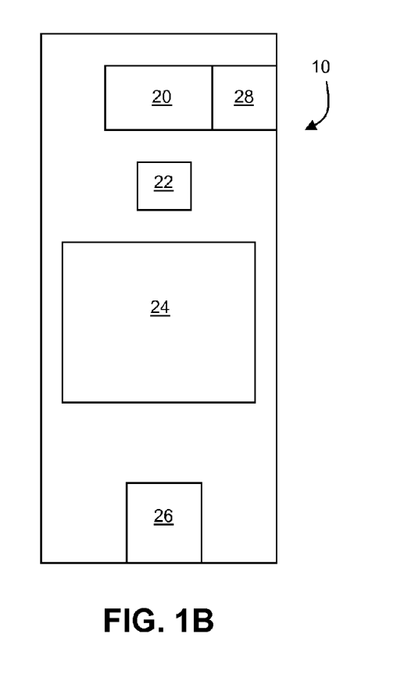

Measurement systems are generally disclosed, for example, in PCT Patent Application Publication No. WO 2010/053617, the entire contents of which are incorporated herein by reference. FIGS. 1A and 1B are schematic diagrams showing bottom and top surfaces, respectively, of a sensor 10 that can measure light from a sample. Sensor 10 includes a spectral detector 12, two short-distance radiation sources 14a and 14b, and six long-distance radiation sources 16a, 16b, 16c, 16d, 16e, and 16f. Detector 12 and radiation sources 14a-b and 16a-f are mounted to circuit board 18. Each of short-distance radiation sources 14a and 14b can include one or more packages, and each package can include one or more elements that produce illumination radiation. Similarly, each of long-distance radiation sources 16a-f can include one or more packages, and each package can include one or more elements that produce illumination radiation.

While FIGS. 1A and 1B show an embodiment of sensor 10 that includes two short-distance sources 14a and 14b and six long-distance sources 16a-f, more generally, sensor 10 can include any number of short-distance radiation sources and any number of long-distance radiation sources. For example, in some embodiments, sensor 10 can include one or more short-distance radiation sources (e.g., two or more short-distance radiation sources, three or more short-distance radiation sources, four or more short-distance radiation sources, five or more short-distance radiation sources, six or more short-distance radiation sources, eight or more short-distance radiation sources, or even more short-distance radiation sources). In certain embodiments, sensor 10 can include one or more long-distance radiation sources (e.g., two or more long-distance radiation sources, three or more long-distance radiation sources, four or more long-distance radiation sources, five or more long-distance radiation sources, six or more long-distance radiation sources, eight or more long-distance radiation sources, or even more long-distance radiation sources).

The short- and long-distance sources in sensor 10 can be directly attached to circuit board 18. That is, the sources can be mounted directly to circuit board 18, rather than being connected to circuit board 18 via electrical wires or cables, or optical fibers. In some embodiments, the short- and long-distance sources can be soldered directly to circuit board 18 (e.g., with no spacer or other element separating the sources and circuit board 18). In certain embodiments, the short- and long-distance sources can also be fixedly attached to circuit board (e.g., mounted on circuit board 18 such that a fixed spatial relationship exists between the sources and circuit board 18). By virtue of the fixed attachment, the sources do not move independently of circuit board 18, as would occur if the sources were attached with a cable or fiber. Instead, the sources are rigidly attached to circuit board 18 so that the position of the sources with respect to circuit board 18 does not change.

In general, each of the short-distance and long-distance radiation sources can include one or more packages (e.g., two or more packages, three or more packages, four or more packages, five or more packages, six or more packages, or even more packages). Each of the packages can include one or more elements that produce illumination radiation (e.g., two or more elements, three or more elements, four or more elements, or even more elements). Further, elements that emit radiation at different wavelengths can be positioned at different spatial locations, depending upon the sample the detector. For example, if detector 12 is configured to resolve different wavelengths at different spatial positions, the elements and/or packages in some or all of the short- and long-distance sources can be positioned to correspond directly or opposingly to the configuration of detector 12.

In some embodiments, the number of packages in some of the short- and/or long-distance radiation sources can vary. For example, sources that are positioned further from detector 12 can include larger numbers of packages, to ensure that sufficient scattered radiation intensity is measured by detector 12. In general, any of the short- and/or long-distance sources can include any number of packages, the number of packages being selected to ensure that the sample is sufficiently illuminated with a desired distribution of incident radiation, and to ensure that detector 12 obtains suitable measurements of scattered radiation from the sample. As an example, in some embodiments, a long-distance source that is positioned furthest from detector 12 can include 1.5 times as many packages (e.g., 2.0 times as many packages, 2.5 times as many packages, 3.0 times as many packages, 3.5 times as many packages, 4.0 times as many packages as a long-distance source that is positioned nearest to detector 12.

The elements within the packages of each short- and long-distance radiation source are typically selected so that, when the elements are activated (e.g., emitting light), the spectrum of the light produced collectively by the elements corresponds to a desired spectral distribution of illumination radiation. The spectral distribution can be altered by positioning particular elements within the short- and/or long-distance sources, so that the sample can be illuminated according to specific spectral distributions. In some embodiments, for example, the illumination spectrum for one or more short- and/or long-distance sources can be selected so that measurement sensitivity of sensor 10 in particular regions of the spectrum is enhanced, as discussed previously.

As shown in FIG. 1A, the emission windows of radiation sources 14$a$-$b$ and 16$a$-$f$, and the radiation entry surface of detector 12, are exposed on the bottom surface of sensor 10.

Sensor 10 also includes an electronic processor 20, an optional applications processor 22, an optional display unit 24, a power source 26, and a communication interface 28. Processors 20 and 22, display 24, power source 26, and interface 28 are mounted to the upper surface of circuit board 18, as shown in FIG. 1B. In some embodiments, processor 22 is not included in sensor 10; instead, processor 22 is part of an external computing device (e.g., a personal computer) that communicates with sensor 10 via communication interface 28, and performs some or all of the functions of processor 22 (or processor 20) disclosed herein.

Figure 2:
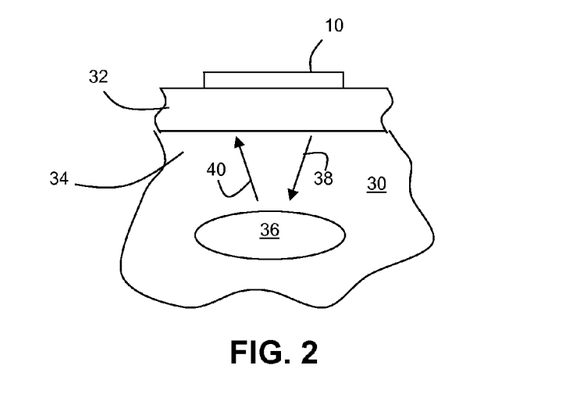
FIG. 2 is a schematic diagram showing a sensor attached to a surface of a sample.

FIG. 2 shows a partial schematic diagram of sensor 10 mounted on a sample 30. Sample 30 includes one or more layers of skin 32, a subcutaneous layer of fat 34, and underlying muscle tissue 36. Sensor 10 is configured to interrogate muscle tissue 36 by directing radiation 38, generated by at least one (e.g., all) of radiation sources 14$a$-$b$ and at least one of the radiation sources 16$a$-$f$, to be incident on muscle tissue 36. Scattered radiation 40 is received and analyzed by detector 12 (FIG. 1A) to determine a spectrum of the scattered radiation. The scattered radiation spectrum is then processed by electronic processor 20 and/or processor 22 (FIG. 1B) to determine an absorbance spectrum of muscle tissue 36. Based on the absorbance spectrum, electronic processor 20 and/or 22 can determine one or more properties of sample 30 (and in particular, of muscle tissue 36 within sample 30).

In general, the scattered radiation spectrum measured by detector 12, which typically includes wavelength-dependent information about scattered radiation from sample 30, can be converted by an electronic processor to an absorbance spectrum of muscle tissue 36 using well-known methods. In the following discussion, reference is made to absorbance spectra of samples such as sample 30. However, the apparatus and methods disclosed herein can also be used to derive reflectance spectra from measured scattered radiation; reflectance and absorbance are related by a simple mathematical transformation. Methods for converting spectral scattered radiation information into reflectance and absorbance spectra for a sample are disclosed, for example, in U.S. Pat. No. 7,532,919.

In addition to converting scattered radiation information into absorbance and/or reflectance spectra, processor 20 and/or 22 can be configured (e.g., using calibration equations and/or data stored in memory units, magnetic storage units, and/or optical storage units) to analyze absorbance spectra to obtain measurements of physiologically important parameters for sample 30. In general, processor 20 and/or 22 can be configured to perform any of the analysis steps that are discussed herein.

In some embodiments, one or more absorbance spectra for sample 30 can be analyzed to determine pH (e.g., muscle tissue pH) in the sample. Systems and methods for determining tissue pH are disclosed, for example, in U.S. Pat. No. 5,813,403.

In certain embodiments, one or more absorbance spectra for sample 30 can be analyzed to determine blood hematocrit in the sample. Systems and methods for determining blood hematocrit are disclosed, for example, in U.S. Pat. No. 6,006,119.

In some embodiments, one or more absorbance spectra for sample 30 can be analyzed to determine quantities such as hemoglobin concentration, and/or water content, and/or oxygen tension and/or tissue oxygen saturation. Systems and methods for determining these quantities are disclosed, for example, in U.S. Pat. No. 6,766,188. Suitable systems and methods are also disclosed, for example, in U.S. Pat. No. 7,532,919.

In certain embodiments, one or more absorbance spectra for sample 30 can be analyzed to determine quantities such as anaerobic threshold and/or metabolic rate (e.g., oxygen consumption rate) in the sample. Systems and methods for determining these quantities are disclosed, for example, in U.S. Patent Application Publication No. US 2009/0024013, the entire contents of which are incorporated herein by reference.

In some embodiments, one or more absorbance spectra for sample 30 can be analyzed to determine additional quantities such as a temperature of a tissue of interest within sample 30. In addition, processor 20 and/or 22 can include a hardware-based temperature monitor that effectively monitors a temperature of the sample surface to which sensor 10 is attached, for example.

General Methodology

As discussed above, numerical algorithms can be used to reduce and/or remove spectral contributions in reflectance spectra that arise from optical property variations in tissues of interest, prior to using the reflectance spectral data in PLS modeling applications to measure analytes of interest. Examples of such algorithms are disclosed in U.S. Pat. No. 7,616,303.

PCA loading corrections can be used to reduce and/or remove contributions to reflectance spectra that arise from analyte-irrelevant variations in optical properties of tissues of interest (e.g., tissues in which analytes of interest are measured). Optical properties that exhibit such variations can include scattering properties, absorption properties, tissue refractive indices, and other properties. In general, variations in infrared absorption by tissues of interest are also related to concentrations of one or more analytes of interest. Accurate measurement of analytes of interest may therefore include determining and correcting for the analyte-irrelevant contributions to reflectance spectra.

PCA analysis can be used to obtain spectral "signatures" of the analyte-irrelevant variations, which can then be removed from the spectral reflectance data via orthogonalization steps. PCA loading corrections can be applied during both calibration and predictive steps to further improve PLS models constructed from the corrected spectral reflectance data. Variations in spectral reflectance measurements that arise from variations in optical properties of tissues of interest can be reduced and/or removed in a series of steps. For example, in some embodiments, a first analysis step includes determining variations in spectral reflectance data that are not relevant to a target analyte by PCA on a set of spectra collected from different subjects (and/or from different locations on the same subject) in the same calibration set with substantially similar values of the analyte. The variations can be expressed as a set of loading vectors of principal spectral components obtained from PCA. The first analysis step is described by Equation 1:

$$X_{0,mc} = X_0 - X_{0,mean} = SP^T + E \qquad (1)$$

In Equation 1, $X_0$ is a matrix with dimensions $m_0 \times n$. Each of the $m_0$ rows of $X_0$ corresponds to a reflectance spectrum recorded for a different sample used for PCA, and n is the number of wavelength points in each reflectance spectrum. The spectra in $X_0$ include analyte-irrelevant spectral reflectance variations. Matrix $X_{0,mean}$ has dimensions $m_0 \times n$ and includes $m_0$ rows, where each row is a $1 \times n$ vector whose elements correspond to the column mean values of $X_0$, so that subtracting $X_{0,mean}$ from $X_0$ yields matrix $X_{0,mc}$ with dimensions $m_0 \times n$, where $X_{0,mc}$ is a mean-centered matrix of $X_0$. S is a PCA score matrix with dimensions $m_0 \times f_0$, where $f_0$ is a number of principal components used to model variations in $X_0$. Matrix P is the PCA loadings matrix and has dimensions $n \times f_0$. Matrix E, with dimensions $m_0 \times n$, is a matrix of spectral residuals of $X_0$ that are not modeled by PCA.

In a second analysis step, spectra used for PLS calibration and spectra used for PLS-based prediction are orthogonalized with respect to the loading vectors of the principal components obtained in the first step. Spectral contributions due to variations in optical properties of the tissues of interest are reduced and/or removed in the corrected spectra which result from the second analysis step. The second analysis step is described by Equation 2:

$$\begin{aligned}X_{ort} &= (X - X_{0,mean(m,n)}) - (X - X_{0,mean(m,n)})P_1 P_1^T + \\ X_{0,mean(m,n)} &= X - (X - X_{0,mean(m,n)})P_1 P_1^T\end{aligned} \qquad (2)$$

In Equation 2, $X_{ort}$ is the orthogonalized (e.g., corrected) spectral matrix with dimensions $m \times n$, where m is the number of samples, e.g., the m rows of $X_{ort}$ correspond to corrected reflectance spectra recorded from m different samples. Matrix X with dimensions $m \times n$ corresponds to m original, uncorrected spectra. Matrix $X_{0,mean(m,n)}$ with dimensions $m \times n$ includes m rows, where each row is a $1 \times n$ vector whose elements correspond to the column mean values of $X_0$. $P_1$, with dimensions $n \times f_1$, is a truncated loadings matrix, where the number of columns $f_1$ is equal to a number of orthogonalization factors used in the orthogonalization procedure. In general, $f_1$ is less than or equal to $f_0$, and a value for $f_1$ is selected on the basis of the element values in the S and P matrices calculated in Equation 2. Following orthogonalization, the corrected reflectance spectra in matrix $X_{ort}$ can be used in PLS calibration and/or modeling to predict values of analytes of interest.

When incident light interacts with a sample, measured light corresponding to light that is reflected from and/or transmitted through the sample is attenuated relative to the incident light. The attenuation $A(\lambda)$ in optical density units at wavelength $\lambda$ is defined as $$A(\lambda) = -\log_{10}\left(\frac{I_1(\lambda)}{I_0(\lambda)}\right) \qquad (3)$$

where $I_0(\lambda)$ and $I_1(\lambda)$ are the intensity of the incident light, and the intensity of light after passing through the sample, respectively. Attenuation A in a range of wavelengths is called the attenuation spectrum.

The attenuation spectrum is related to the reflectance spectrum $R(\lambda)$ of the sample according to $A = \log_{10}(1/R)$. Reflectance spectra can be measured for a wide variety of different subjects—corresponding to relatively broad ranges of different sample analyte values and properties—and these measured reflectance spectra can be used to determine PCA correction factors.

However, as discussed above, the measurement of data from such a large number of human subjects can be both time consuming and expensive. Moreover, in some cases, it can be difficult to obtain data over a wide range of certain sample parameters. For example, it can be difficult—and even dangerous—to manipulate experimental conditions to collect spectra from human subjects at a wide range of different muscle tissue pH values, as many human biochemical processes are very sensitive to pH. The present disclosure therefore provides methods and systems for calculating reflectance spectra reflecting a wide variety of different sample analyte values and properties, and determining PCA correction factors from the calculated reference spectra. The PCA correction factors can then be used to correct some or all of the calculated reference spectra to reduce variations due to contributions that do not correspond to analytes of interest. The methods and systems are further described, for example, in Zou et al., "Feasibility of analyte prediction in phantoms using a theoretical model of near-infrared spectra," Proc. of SPIE Vol. 7572, 757201-1-757201-9 (2010), the entire contents of which are incorporated by reference herein.

Suitable methods for calculating sample reflectance spectra are disclosed, for example, in the following references, the entire contents of each of which is incorporated by reference herein: Kienle et al., J. Opt. Soc. Am. A 14: 246-257 (1997); Kienle et al., Appl. Opt. 37: 779-791 (1998); and Liemert et al., J. Biomed. Opt. 15: 025003-1-025003-10 (2010). Kienle et al. use a two layer turbid model for photon diffusion to describe sample reflectivity. In this model, a muscle layer includes an analyte of interest, and another layer (e.g., a fat layer) overlies the muscle layer. Kienle et al. show, using the "EBCF" boundary condition, that for a two-layer turbid medium, the reflectance R at distance $\rho$ between a light source and a detector is calculated as follows:

$$R(\rho) = \int_{2\pi} d\Omega [1 - R_{fres}(\theta)] \frac{1}{4\pi} 3D_1 \frac{\partial \Phi_1(\rho, z=0)}{\partial z} \cos^2\theta \quad (4)$$

where $\Phi_1$ is the fluence rate in the outer (illuminated) layer, $$D_1 = \frac{1}{3(\mu'_{s,1} + \mu_{a,1})} \quad (5)$$

is the diffusion constant in that layer, and $R_{fres}(\theta)$ is the Fresnel reflection coefficient for a photon with an incident angle $\theta$ relative to the normal to the boundary. Since $d\Omega = \sin\theta\, d\phi\, d\theta$, where $0 \leq \theta \leq \pi/2$ (in this analysis only diffuse radiation leaving the top layer is treated), and $\phi$ is the azimuth ($0 \leq \phi \leq 2\pi$), Equation (4) can be written as:

$$R(\rho) = \frac{3D_1}{2} \frac{\partial \Phi_1(\rho, z=0)}{\partial z} \int_0^{\frac{\pi}{2}} [1 - R_{fres}(\theta)] \cos^2\theta \sin\theta\, d\theta. \quad (6)$$

The quantity $$\frac{\partial \Phi_1(\rho, z=0)}{\partial z}$$

can be calculated. According to Kienle et al., $$\Phi_1(\rho, z) = \frac{1}{2\pi} \int_0^\infty \phi_1(z, s) s J_0(s\rho) ds \quad (7)$$

where $\phi_1$ is a Fourier transform of the fluence function and $J_0$ is the zeroth-order Bessel function. Therefore, $$\frac{\partial \Phi_1(\rho, z)}{\partial z} = \frac{1}{2\pi} \int_0^\infty \frac{\partial \phi_1(z, s)}{\partial z} s J_0(s\rho) ds \quad (8)$$

Near $z=0$ (with $z>0$), the formulae in Kienle et al. imply that $$\frac{\partial \phi_1(z, s)}{\partial z} = \quad (9)$$

$$\frac{\cosh(\alpha_1(z_0 - z))}{D_1} - \frac{\sinh(\alpha_1(z_b + z_0))}{D_1} \begin{pmatrix} D_1\alpha_1\sinh(\alpha_1(l - z)) + \\ D_2\alpha_2\cosh(\alpha_1(l - z)) \\ \overline{D_1\alpha_1\cosh(\alpha_1(l + z_b)) +} \\ D_2\alpha_2\sinh(\alpha_1(l + z_b)) \end{pmatrix}$$

with distances $z_0$ and $z_b$ defined as in Kienle et al. At $z=0$, Equation (9) is (left-) continuous, and so $$\frac{\partial \phi_1(z=0, s)}{\partial z} = \quad (10)$$

$$\frac{\cosh(\alpha_1 z_0)}{D_1} - \frac{\sinh(\alpha_1(z_b + z_0))}{D_1} \begin{pmatrix} D_1\alpha_1\sinh(\alpha_1 l) + \\ D_2\alpha_2\cosh(\alpha_1 l) \\ \overline{D_1\alpha_1\cosh(\alpha_1(l + z_b)) +} \\ D_2\alpha_2\sinh(\alpha_1(l + z_b)) \end{pmatrix}$$

where $$\alpha_j^2 = (D_j s^2 + \mu_{a,j})/D_j, \quad D_j = \frac{1}{3(\mu'_{s,j} + \mu_{a,j})},$$

($j=1, 2$) and $l$ is the fat thickness.

Combining these equations, Equation (4) now becomes $$R(\rho) = \frac{3}{4\pi} \int_0^{\frac{\pi}{2}} [1 - R_{fres}(\theta)]\cos^2\theta \sin\theta\, d\theta \times \quad (11)$$

$$\int_0^\infty \left( \cosh(\alpha_1 z_0) - \sinh(\alpha_1(z_b + z_0)) \begin{pmatrix} D_1\alpha_1\sinh(\alpha_1 l) + \\ D_2\alpha_2\cosh(\alpha_1 l) \\ \overline{D_1\alpha_1\cosh(\alpha_1(l + z_b)) +} \\ D_2\alpha_2\sinh(\alpha_1(l + z_b)) \end{pmatrix} \right)$$

$$s J_0(\rho s) ds$$

From Equation (11), it is evident that for a two-layer fat and muscle sample, the reflectance actually includes two parts. One part is the first integration which is related to the surface of the fat layer and the optical device, and the second part is the second integration which is related to the fat layer and the muscle layer. The first integral $$\int_0^{\frac{\pi}{2}} [1 - R_{fres}(\theta)]\cos^2\theta \sin\theta\, d\theta \quad (12)$$

can be calculated when the refractive index $n_j$ (j=1, 2) is known above and below the surface layer. Several methods can be used to calculate the second integral. For example, in some embodiments, the general composite rectangle method (Equation (13))

$$\int_0^N f(x)dx \approx \sum_{j=1}^{N} f(x_j)\Delta x \tag{13}$$

can be used to calculate the second integral. To perform the second integration in Equation (11), a value of N is selected such that $$\int_0^\infty \left( \cosh(\alpha_1 z_0) - \sinh(\alpha_1(z_b + z_0)) \frac{\begin{array}{l} D_1\alpha_1\sinh(\alpha_1 l) + \\ D_2\alpha_2\cosh(\alpha_1 l) \\ \hline D_1\alpha_1\cosh(\alpha_1(l+z_b)) + \\ D_2\alpha_2\sinh(\alpha_1(l+z_b)) \end{array}} \right) sJ_0(\rho s)ds = \tag{14}$$

$$\int_0^N \left( \cosh(\alpha_1 z_0) - \sinh(\alpha_1(z_b + z_0)) \frac{\begin{array}{l} D_1\alpha_1\sinh(\alpha_1 l) + \\ D_2\alpha_2\cosh(\alpha_1 l) \\ \hline D_1\alpha_1\cosh(\alpha_1(l+z_b)) + \\ D_2\alpha_2\sinh(\alpha_1(l+z_b)) \end{array}} \right) sJ_0(\rho s)ds + E$$

and the error term E is as small as possible. Then, the interval [0, N] is separated into a set of small sub-intervals and Equation (13) is used to approximately evaluate the integral in each sub-interval. Because the value of the integral in Equation (14) is typically small (e.g., less than $10^{-5}$ for each wavelength), the sub-intervals can be set short enough to get relatively small approximation errors. For example, in some embodiments, N can be set to 150, the interval [0, 150] can be equally set into 15000 sub-intervals, and the middle point of each subinterval can be selected in Equation (13).

The zeroth-order Bessel function $J_0(x)$ oscillates around zero so that it is possible, with certain selections of sample points, the value of the integral in Equation (14) is negative. However, it is known that $R(\rho)$ is always positive-valued, and the integration in Equation (12) is always positive, so the integration in Equation (14) should be positive as well. According to Mastroianni et al., "Truncated Gauss-Laguerre Quadrature Rules," in *Recent Trends in Numerical Analysis* (Nova Science, 2000), pp. 213-222, it is possible that the integration in [0, M], where M<N, is more accurate than that in [0, N]. Therefore, instead of calculating the integral in Equation (14) over the whole interval [0, N], the integral is calculated over [0, M], where M (≤N) is the largest value such that the integration in Equation (14) on [0, M] is positive (for all wavelengths).

Thus, by using the methods discussed above, reference spectra spanning a wide range of different sample analyte values and parameters can be determined. To generate such reference spectra, different sample values and parameters can be varied to yield variations in certain sample properties. In general, sample-to-sample variations are attributable to variations in scattering and absorbance (reflectance) among different samples. Scattering and absorbance, in turn, depend upon certain sample parameters that can be systematically varied during calculation of the reference spectra. For example, sample absorbance is a function of hemoglobin concentration and hemoglobin oxygen saturation. In turn, hemoglobin oxygen saturation is a function of oxygen tension, pH, temperature, and carbon dioxide partial pressure. Varying the values of some or all of these properties, in turn, yields a multi-dimensional set of reference spectra that correspond, along individual dimensions, to isolated variations of each of these properties while keeping the others constant. Each of the parameters can be varied over a wide range of values; in many cases, over a range of values that is wider than would be possible to measure in human test subjects.

As an example, the absorption coefficient $\mu_a(\lambda)$ for a sample as a function of wavelength $\lambda$ can be expressed in terms of absorption of light by hemoglobin and water, which are major choromophores inside the sample $$\mu_a(\lambda)=[c_{HHb}\epsilon_{HHb}(\lambda)+c_{O_2Hb}\epsilon_{HbO_2}(\lambda)+c_{wat}\epsilon_{wat}(\lambda)] \tag{15}$$

where $c_{HHb}$, $c_{O2Hb}$ and $c_{wat}$ are the concentrations of deoxygenated hemoglobin, oxygenated hemoglobin, and water in the tissue respectively, and $\epsilon_{HHb}(\lambda)$, $\epsilon_{O2Hb}(\lambda)$, and $\epsilon_{wat}(\lambda)$ are wavelength-dependent extinction coefficients for HHb, $O_2$Hb and water respectively. In this example, hemoglobin and myoglobin are assumed to be indistinguishable.

From Equation (15), if $\epsilon_{HHb}(\lambda)$, $\epsilon_{O2Hb}(\lambda)$, and $\epsilon_{wat}(\lambda)$ are known (and values for these parameters can be obtained from literature or measurement), and if $c_{HHb}$, $c_{O2Hb}$ and $c_{wat}$ are also known, then $\mu_a$ can be determined. Typically, the water concentration $c_{wat}$ is fixed at 60% by volume, and only $c_{HHb}$ and $c_{O2Hb}$ are varied to introduce variation in $\mu_a$.

The concentrations $c_{HHb}$ and $c_{O2Hb}$ are also typically dependent on the total hemoglobin (THb) concentration $c_{THb}$ which is the sum of $c_{HHb}$ and $c_{O2Hb}$, and the hemoglobin oxygen saturation $SO_2$; the relationship is described by Equation (16):

$$SO_2 = \frac{c_{O_2Hb}}{c_{O_2Hb}+c_{HHb}} = \frac{c_{O_2Hb}}{C_{THb}} \tag{16}$$

Thus, if $c_{THb}$ and $SO_2$ are known, then $c_{O2Hb}$ and $c_{HHb}$ can be obtained from Equations (17) and (18) according to:

$$C_{O_2Hb}=SO_2 \ast C_{THb} \tag{17}$$

$$C_{HHb}=C_{THb}-C_{O_2Hb} \tag{18}$$

As a further example, various blood and tissue parameters can cause $SO_2$ to vary in different samples. As discussed above, variations in $SO_2$ can cause changes in values of $c_{O2Hb}$ and $c_{HHb}$, which in turn can lead to changes in $\mu_a(\lambda)$ and in the attenuation spectrum $A(\lambda)$ of a sample. The oxygen-hemoglobin dissociation curve describes the relationship between oxygen tension expressed in partial pressure of oxygen $O_2$ ($pO_2$) and hemoglobin oxygen saturation $SO_2$. The dissociation curve is shifted under different physiological conditions but, in general, its shape remains approximately the same. Variations in values of tissue parameters such as pH, temperature, partial pressure of carbon dioxide ($pCO_2$), and $pO_2$ that affect hemoglobin $SO_2$ can be related by the oxygen-hemoglobin dissociation curve under different physiological conditions.

Under standard physiological condition (e.g., pH of 7.4, $pCO_2$ of 40 mmHg, and temperature of 37° C.), the relationship between the $pO_2$ and $SO_2$ can be described by Equation (19):

$$SO_2=(23400 \ast (pO_2\_vir^3+150 \ast pO_2\_vir)^{-1}+1)^{-1} \tag{19}$$

where $pO_2\_vir$ is $pO_2$ in units of Torr under standard physiological condition, and $SO_2$ is hemoglobin oxygen saturation (in a range from 0 to 1). Under non-standard physiological conditions, Equation (20) can be used to convert the actual $pO_2$ ($pO_2\_act$) to its value $pO_2\_vir$ under standard physiological conditions:

$$pO_2\_vir = pO_2\_act * 10^{(0.024*(37-T)+0.4*(pH-7.4)+0.06*(\log 10(40) - \log 10(pCO^2)))} \quad (20)$$

where T is temperature in degrees Celsius, pH represents the pH of the sample, and $pCO_2$ is the partial pressure of carbon dioxide in the sample under actual physiological conditions. Carbon dioxide partial pressure $pO_2$ (both $pO_2\_vir$ and $pO_2\_act$) and $pCO_2$ are expressed in units of mm Hg in Equation (20).

Thus, when pH, temperature, $pCO_2$, and $pO_2$ under the actual physiological conditions ($pO_2\_act$) are known, $pO_2$ under standard physiological conditions ($pO_2\_vir$) can be obtained from Equation (20). Once known, $pO_2\_vir$ can be used to calculate $SO_2$ using Equation (19). Moreover, by varying ranges of the sample parameters pH, temperature, $pO_2$, $pCO_2$ and $C_{THb}$ within physiological and pathophysiological ranges of values, a range of absorption coefficient values $\mu_a$ can be obtained, which can be used in combination with a range of reduced scattering coefficient values $\mu_s$ to calculate attenuation spectra A that correspond to a wide range of different analyte values and sample properties.

To test the range of different values of $pO_2\_vir$ that can be produced via Equation (20), values of pH, temperature, $pCO_2$, $pO_2\_act$, $c_{THb}$, and $c_{wat}$ were varied by choosing a series of values of each parameter within the following intervals to generate different values of $pO_2\_vir$: pH (6.5-8.0), temperature (25.0-40.0° C.), $pCO_2$ (10.0-215.0 mm Hg), $pO_2\_act$ (0.0-100.0 mm Hg), $c_{THb}$ (0.01-0.25 or 0.01-0.2 mM), and $c_{wat}$ (volume fraction 0.6). Using different combinations of these parameters, $pO_2\_vir$ was calculated from Equation (20). For some combinations, for example, $pO_2\_vir$ calculated from Equation (20) fell outside the physiological range of $pO_2$, so the spectra and the corresponding tissue parameters with $pO_2\_vir$ greater than 100 mm Hg were removed from the simulated reference spectra and were not used to calculate models for sample analytes. In general, the $pO_2\_vir$ threshold can be established at any pressure value that is convenient and/or yields accurate measurement results; for example, the $pO_2\_vir$ threshold can be established at 120 mm Hg instead of 100 mm Hg. The water concentration (volume fraction) was fixed as 0.6, which is suitable for normal muscle; this value can be changed (e.g., when water concentration is an analyte to be determined).

In similar fashion, different values of the reduced scattering coefficient $\mu_s'$ can be calculated according to the equation $$\mu_s'(\lambda) = a\lambda \times 10^{-3} + b \quad (21)$$

where a, b are slope and intercept constants respectively and are different for different samples and/or human subjects.

Figure 3:
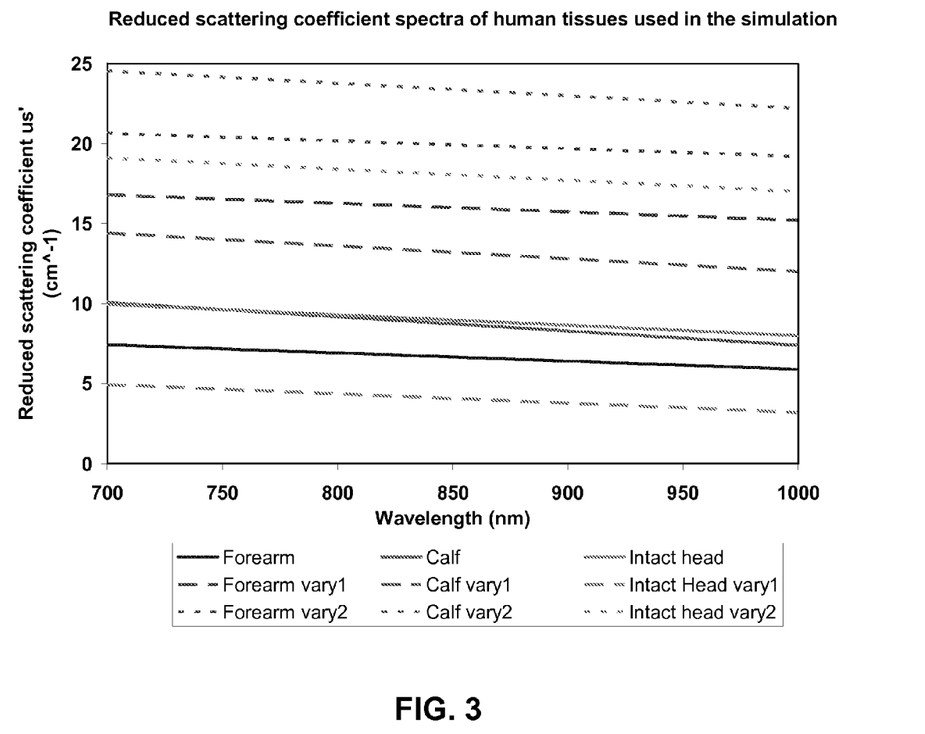
FIG. 3 is a plot showing different values of reduced scattering coefficients produced by varying sample parameters.

Tissue scattering physiological ranges are generally known from literature sources. To evaluate the production of different reduced scattering coefficient values, a range of $\mu_s'$ values used in calculating reference spectra were calculated according to Equation (21). As starting points in these calculations, the wavelength dependent scattering coefficients for the forearm, calf and intact head were used. Since several levels of scattering coefficient are needed to develop a robust calibration model, the intercept a and the slope b in Equation (21) were varied to produce nine $\mu_s'$ spectra that covered the sample scattering physiological range (around 5-25 cm$^{-1}$ at 700 nm).

FIG. 3 shows the plot of $\mu_s'$ versus $\lambda$ for forearm, calf, intact head and other $\mu_s'$ spectra obtained by varying one or more of the parameters associated with the sample. More specifically, in FIG. 3, reduced scattering coefficients taken from literature sources (forearm, calf, intact head) are shown as solid lines; reduced scattering coefficients obtained by varying parameters a and b in Equation (21) are shown as dotted lines. By choosing values of a and b appropriately, reduced scattering coefficients that cover a physiological range from 5-25 cm$^{-1}$ at 700 nm can be produced.

Figure 4:
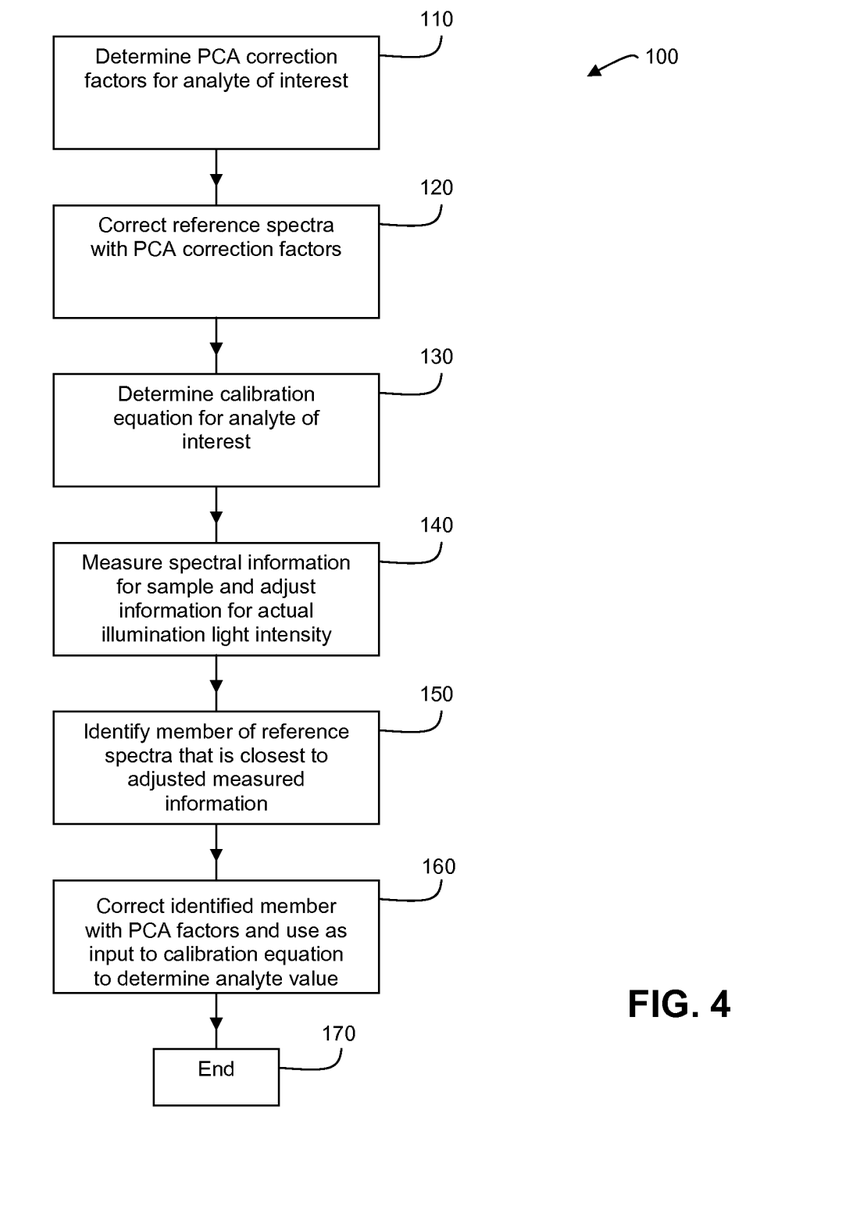
FIG. 4 is a flow chart that includes a series of steps for using calculated reference spectra to determine sample analyte values.

FIG. 4 shows a flow chart 100 that includes a series of steps for using the calculated reference spectra, determined according to the methods discussed above, for example, to determine sample analyte values. In first step 110, PCA loading correction factors are determined for one or more analytes of interest. The determination of the loading factors proceeds according to the methods discussed previously, for example. In some embodiments, all calculated reference spectra are used in the determination of PCA correction factors. In certain embodiments, a subset of the calculated reference spectra may be selected and used to determine the PCA correction factors.

In second step 120, the PCA correction factors are applied to the reference spectra (or a subset thereof) to correct the calculated reference spectra. PCA loading correction factors can be determined each time analyte values are to be measured. Alternatively, or in addition, some or all of the PCA loading factors can be stored in a memory unit. When analyte values are to be measured, the stored PCA loading factors can be retrieved from memory and used to correct reference spectra. Moreover, some or all of the corrected reference spectra can also be stored in a memory unit and retrieved as needed for determination of analyte values.

Next, in optional step 130, the corrected reference spectra are used to determine parameters for a model for the analyte of interest based on spectral information. For example, methods such as PLS regression can be used to calculate various model parameters. Methods and systems for PLS-based model calculation are disclosed, for example, in U.S. Pat. No. 5,813,403.

To determine parameters for a PLS model, in some embodiments, different subsets of the reference spectra can be selected, each subset corresponding to a different value of a particular analyte of interest. Each of the different subsets of reference spectra are then corrected using PCA loading correction factors (if this has not already occurred in step 120 above), and each corrected subset of spectra is used in a PLS regression procedure to determine PLS model parameters. The determined PLS model parameters are used with the PLS model for the analyte of interest to predict one or more values of the analyte (e.g., a concentration of the analyte) based on the selected subset of spectra. The PLS predictive procedure yields an error term associated with predicting the value of the analyte. For each subset of reference spectra, an associated error term is determined. Then, the subset of reference spectra with the lowest associated error term (the subset corresponding to a common value of the analyte, as discussed above) is identified and used in subsequent determinations of values for the particular analyte of interest. In some embodiments, different subsets of reference spectra are used to determine values of different analytes. These different subsets of reference spectra can be stored (or information about them can be stored) in a memory unit for use in subsequent measurements of analyte values.

In step 140, spectral information for a sample (e.g., muscle tissue in a human subject) is measured, e.g., in the form of a reflectance spectrum for the sample. The measured spectral information can be adjusted by a scaling factor (e.g., a multiplicative scaling factor and/or an additive offset factor) to account for variations in measurement light intensity.

Next, in step 150, the adjusted measured spectral information is compared against the (uncorrected) reference spectra to determine which of the reference spectra is closest to the measured spectrum of the sample. A variety of different methods can be used to determine the closest reference spectrum. In some embodiments, for example, the closest reference spectrum is identified as the reference spectrum for which a maximum difference between the measured and reference spectra, and a minimum difference between the measured and reference spectra, is smallest:

$$a_{s_0}(\lambda) = \min_{a_s \in S_s}(\max_\lambda(a_{m_0}(\lambda) - a_s(\lambda)) - \min_\lambda(a_{m_0}(\lambda) - a_s(\lambda))) \quad (22)$$

In step 160, the identified reference spectrum is corrected using the PCA correction factors determined in step 110 and used as input to a calibration equation that relates spectral information to values of the analyte. In some embodiments, the calibration equation can be previously determined and stored (e.g., parameter values stored) in a memory unit connected to electronic processor 20 and/or application processor 22. Alternatively, or in addition, the calibration equation's parameters can be partly or fully determined in step 130, and the corrected reference spectral information can be used as input to the calibration equation determined in step 130 to obtain values associated with one or more analytes in the sample.

In the preceding discussion, the calibration equation was described as an equation determined using a procedure such as PLS regression. In some embodiments, the calibration equation can be another type of equation. For example, the calibration equation can include a Taylor series expansion of a measurable sample quantity such as absorbance or reflectance in terms of one or more analytes present in the sample. The one or more analytes can include, for example, pH, temperature, oxygen tension, oxygen saturation, carbon dioxide partial pressure, hemoglobin concentration, water concentration, and hematocrit. Suitable methods for constructing and evaluating such Taylor series expansion-based calibration equations are disclosed, for example, in U.S. Pat. No. 7,532,919.

The overall process in flow chart 100 then terminates at step 170. Using the process shown in FIG. 4, reference spectral data that incorporates a wide range of sample variability can be generated without measurement data from human subjects. Further, PCA correction factors can be calculated from the simulated spectra, and the simulated spectra can be corrected with the determined PCA factors. Calibration equations for sample analytes can be determined using the corrected reference spectra, and without using spectral information measured from human subjects. Further, sample analyte values can be determined by using reference spectral information as input into a suitable calibration equation.

EXAMPLES

The disclosure is further described in the following examples, which are not intended to limit the scope of the disclosure.

Example 1

To evaluate the overall accuracy and speed of determination of analyte values using the methods and systems disclosed herein, a set of India ink (Scientific Device Lab Inc., Des Plaines, Ill.) solid phantoms were produced. Ten mimic-muscle solid phantoms and three mimic-fat solid phantoms were fabricated. Muscle phantoms were made with five ink concentrations which ranged from 0.0037% to 0.0197% and two nominal $\mu_{s0}'$ values of 7 and 9 cm$^{-1}$ at 800 nm; fat phantoms were fabricated with thicknesses of 4, 5, and 6 mm with a nominal $\mu_{s0}'$ value of 12 cm$^{-1}$ at 800 nm. The muscle phantoms were fabricated from India ink, Intralipid (Baxter Healthcare Corp., Deerfield, Ill.), agar (Sigma Chemical Comp., St. Louis, Mo.), and distilled water; the fat phantoms were fabricated from Intralipid, agar, and distilled water. The nominal $\mu_a$ at 800 nm, nominal $\mu_{s0}'$ at 800 nm, and ink concentrations for the muscle phantoms are shown in Table 1. The phantoms were prepared according to procedures disclosed in Cui et al., Proceedings of the SPIE 1431: 180-191 (1991), and in Cubeddu et al., Phys. Med. Biol. 42: 1971-1979 (1997). Parameters (e.g., values of scattering coefficients and/or absorption coefficients) for the samples are shown in Table 1.

TABLE 1

| Phantom | Nominal $\mu_a$ (cm$^{-1}$) | Nominal $\mu_{s0}'$ (cm$^{-1}$) | Ink Conc. (vol. %) | Ink Conc. (vol. %) | Nominal $\mu_{s0}'$ (cm$^{-1}$) | Nominal $\mu_a$ (cm$^{-1}$) | Phantom |
|---|---|---|---|---|---|---|---|
| 1 | 0.05 | 7 | 0.0037% | 0.0037% | 9 | 0.05 | 6 |
| 2 | 0.1 | 7 | 0.0077% | 0.0077% | 9 | 0.1 | 7 |
| 3 | 0.15 | 7 | 0.0117% | 0.0117% | 9 | 0.15 | 8 |
| 4 | 0.2 | 7 | 0.0157% | 0.0157% | 9 | 0.2 | 9 |
| 5 | 0.25 | 7 | 0.0197% | 0.0197% | 9 | 0.25 | 10 |

All phantoms, each of which included a single fat layer atop one of the muscle layers, were illuminated using a tungsten lamp (model 7106-003, Welch Allyn Corp., Skaneateles, N.Y.) as a radiation source and a spectrometer (USB2000, Ocean Optics Inc., Dunedin, Fla.) as the detector. Both the source and detector were coupled into fiber bundles and near the top of the fat layer with a separation of 30.0 mm. Spectra were collected in reflectance mode and converted to absorbance by referencing to a 99% reflectance standard (Labsphere Inc., North Sutton, N.H.).

To predict ink concentrations in the phantoms, a large set of simulated spectra was generated using the methods disclosed herein. Model parameters encompassed a range of parameters used to fabricate the phantoms. The reduced scattering coefficient, $\mu_s'(\lambda)$, a function of $\mu_{s0}'$, was calculated using equations disclosed in Stavaren et al., Appl. Opt. 30: 4507-4514 (1991). The set of simulated spectra, $S_s$, were corrected with an offset term that adjusted for differences between actual light intensity and light intensity measured using the 99% reflectance standard reference. Instead of directly using the simulated spectra to develop a PLS regression model for ink concentration, the principal component analysis loading correction method was first used to correct $S_s$ for spectral variations related to fat thickness and muscle scattering, resulting in loading corrected simulated spectra $S_c$. $S_c$ and the corresponding ink concentrations were then used to produce a PLS model. The number of PLS factors was selected using the cross-validation method described, for example, in Haaland et al., Anal. Chem. 60: 1193-1202 (1998); up to 3 PCA correction factors and 20 PLS factors were considered.

The PLS-based model developed from the corrected spectra ($S_c$) was tested on the set of measured 2-layer phantom spectra, $S_m$. Rather than using $S_m$ directly as input to the PLS model, simulated spectra in the set of the $S_s$ spectra which were the best match to the measured absorbance $S_m$ for each phantom were identified and used as input to the PLS-based model. The best-match calculation was performed according to Equation (22). The best-matched simulated spectra were then corrected with the PCA correction factors derived from the simulated set of spectra used in the PLS model to predict ink concentrations. The PLS model was evaluated by comparing the PLS-estimated ink concentration to the actual ink concentrations by calculating the coefficient of determination ($R^2$) and the root mean square error of prediction (RMSEP).

A total of 5733 reference spectra were calculated, encompassing the range of parameters used to construct the 2-layer phantoms. The PLS model (e.g., a calibration equation) was tested on a set of 30 calculated spectra created using the values for the measured ink concentrations, $H_2O$ concentrations, and nominal $\mu_s$'s for the phantoms. The PLS model, with 2 PCA loadings and 10 PLS factors, resulted in $R^2$ of 0.998 and RMSEP between the actual and predicted ink concentrations of 0.00028%. These results illustrate that the methodology works well on test spectra that match the simulated spectra.

Figure 5:
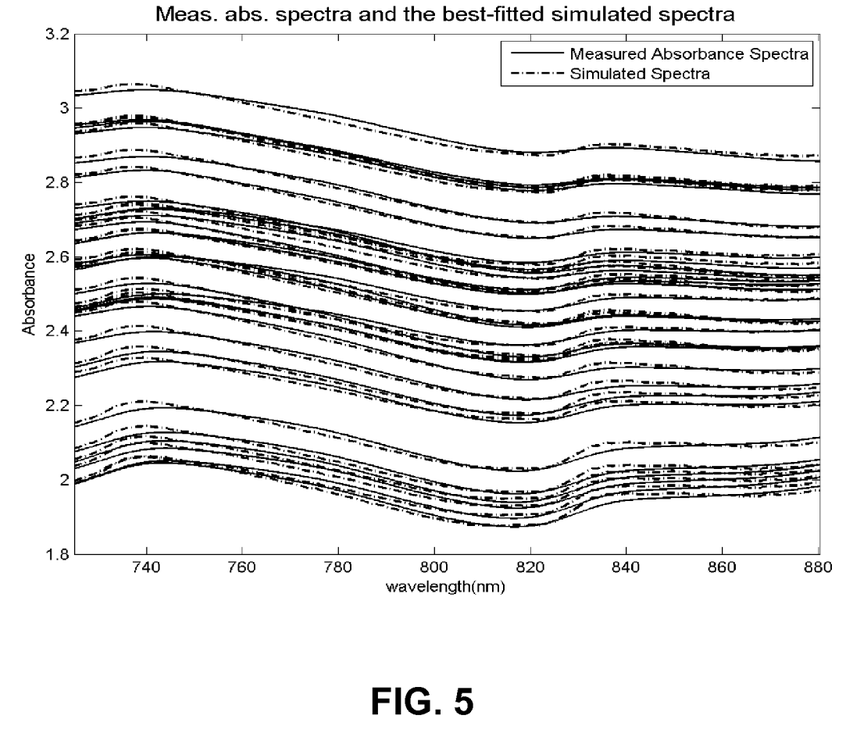
FIG. 5 is a plot showing measured and calculated absorbance spectra for tissue phantoms.

When measured phantom spectra were tested directly in the PLS model constructed from calculated reference spectra, an intermediate step was added to find the reference spectrum that best matched the measured spectrum. Equation (22), discussed above, was used for this purpose. The best-matched calculated spectrum was then corrected with the PCA correction factors and used in the PLS calibration equation created from the 5733 PCA corrected spectra. For the 30 measured phantoms, both the measured and best-matched spectra are shown in FIG. 5; solid lines correspond to measured phantom absorbance spectra, and dotted lines correspond to best-matched reference spectra. There is generally good agreement between the measured and calculated spectra.

Figure 6A:
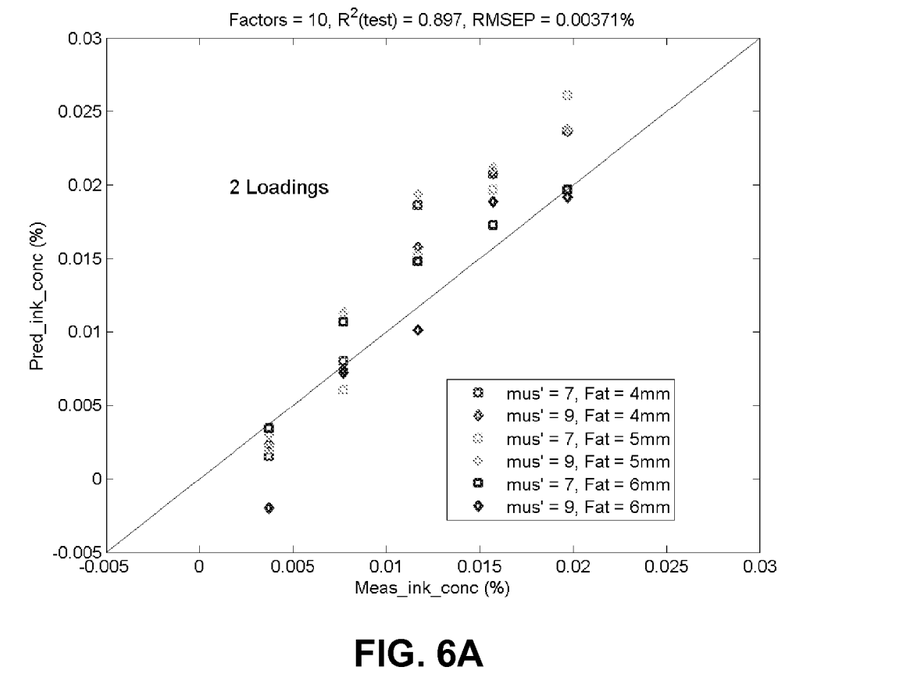
FIG. 6A is a plot showing correlations between predicted and measured ink concentrations for tissue phantoms.

The best matched spectra were evaluated in the PLS model, resulting in an $R^2$=0.897 and RMSEP=0.00371%. FIG. 6A shows a plot of the ink concentration predicted from the best-matched phantom spectra as a function of the measured ink concentration. There is a clear trend between the predicted and actual ink concentrations. The effects of the matrix scattering coefficient ($\mu_s'$) and the fat thickness were explored to examine the source of prediction error using 2-way analysis of variance (ANOVA) for the difference, $\Delta$, between the measured and predicted ink concentrations. Table 2 shows that neither $\mu_s'$, fat thickness, nor the interaction between the two were significantly associated with the error ($\Delta$), since all p values were greater than 0.05.

TABLE 2

| Source | Sum of Squares | DF | Mean Square | F | P |
|---|---|---|---|---|---|
| Fat_Thickness | 0.0000461 | 2 | 0.000023 | 2.41 | 0.111 |
| $\mu_s'$ | 0.00000116 | 1 | 0.00000116 | 0.121 | 0.731 |
| Fat_Thickness*$\mu_s'$ | 0.0000245 | 2 | 0.0000122 | 1.281 | 0.296 |

Figure 6B:
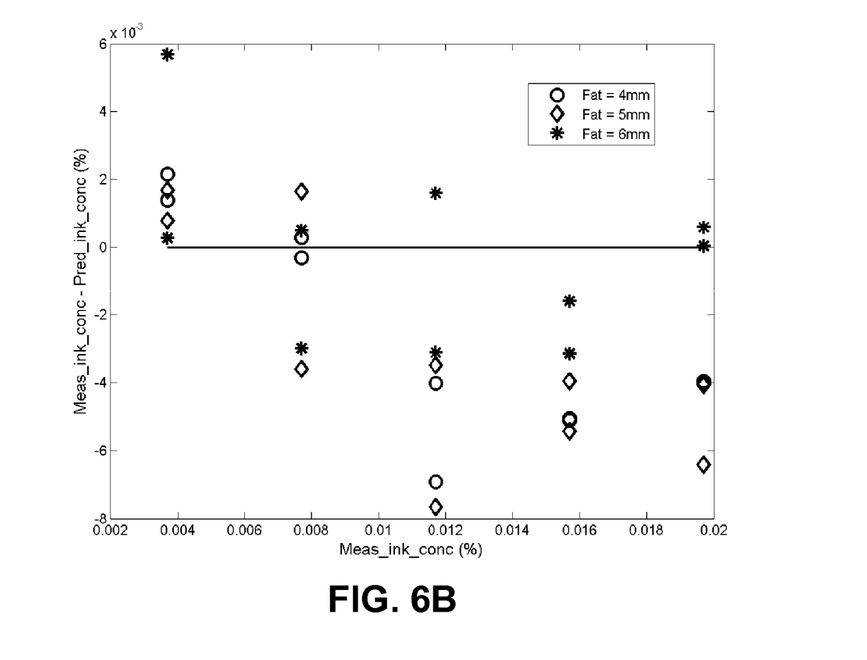
FIG. 6B is a plot showing differences between measured and predicted ink concentrations as a function of fat layer thickness for tissue phantoms.

FIG. 6B is a plot of the difference between the measured and predicted ink concentration as a function of the measured ink concentration, where the results are organized by fat thickness. The results for a fat thickness of 6 mm are closer to zero, and therefore more accurate, than for phantoms with thinner fat layers, suggesting that other methods for simulating spectra for two-layer phantoms may be useful when the fat later in such phantoms is relatively thin, and where there is likely to be more scattering interaction between the muscle and fat layers. Nonetheless, the absorbance spectra collected from phantoms agreed well with calculated reference spectra produced from a two-layer turbid model for photon diffusion. Ink concentrations were well predicted by calibration equations calculated from the reference spectra, providing further evidence that simulated spectra can be effectively used to correct for inter-subject spectral differences, and to determine quantitative values associated with analytes in many samples.

Example 2

To demonstrate the accuracy with which physiologically relevant quantities can be determined using the methods and systems disclosed herein, theoretical near-infrared spectra were simulated for use in predicting total hemoglobin (HbT) and Hematocrit (Hct) values. In particular, the simulated spectra were divided into two sets: a first set of simulated spectra used to train a PLS model for prediction, and a second set of simulated spectra acting as the "experimental" data. A large set of training spectra was used to train a PLS model for HbT prediction. The trained model was then applied to a small set of simulated testing spectra. Both the training and testing sets of spectra were corrected using principal component analysis (PCA) loading correction, as discussed above. Further, before performing the PCA loading correction, the magnitudes of the spectra were scaled down by normalizing against the mean values of the spectra, to ensure that the spectral values were of similar magnitude to real, experimentally obtained spectra.

Training and testing spectra were simulated using one of two models. For samples with no fat layer (e.g., a fat thickness of 0 mm), the one-layer model of Farrell et al. was used. This model is described in more detail, for example, in Farrell et al., Med. Phys. 19: 879-888 (1992), the entire contents of which are incorporated by reference herein. For samples with a fat layer (e.g., a fat thickness >0 mm), the Kienle two-layer turbid media model discussed above was used.

To simulate spectra for the theoretical sample under consideration in this example (a muscle tissue layer with a fat layer of adjustable thickness), the absorbance coefficient of the muscle layer was assumed to be accurately described in terms of absorption from a background contribution ("back") and a tube contributions ("tube"). This model is described in more detail in Liu et al., Med. Phys. 22: 1209-1216 (1995), the entire contents of which are incorporated herein by reference. The absorbance coefficient of the muscle layer, $\mu_{a,sys}(\lambda)$, can therefore be expressed as $$\mu_{a,sys}(\lambda)=(1-f)\mu_{a,back}(\lambda)+f\mu_{a,tube}(\lambda) \quad (23)$$

where the absorbance coefficient of the background contribution, $\mu_{a,back}(\lambda)$, can be expressed as $$\mu_{a,back}(\lambda)=c_{Mb}\epsilon_{Hb}(\lambda)+c_{MbO2}(\lambda)+c_{H2O}\epsilon_{H2O}(\lambda) \quad (24)$$

and where the absorbance coefficient of the tube contribution, $\mu_{a,tube}(\lambda)$, can be expressed as $$\mu_{a,tube}(\lambda)=c_{Hb}\epsilon_{Hb}(\lambda)+c_{HbO2}\epsilon_{HbO2}(\lambda)+c_{H2O}\epsilon_{H2O}(\lambda) \quad (25)$$

In Equations (23)-(25), f is the volume ratio of tubes (e.g., capillaries, venules, arterioles) to the total capillary-tissue volume. The quantity c, corresponds to the concentration of component x, while the quantity $\epsilon_x$ corresponds to the extinction coefficient of component x. The components x include myoglobin (Mb), hemoglobin (Hb), oxygenated myoglobin (MbO2), oxygenated hemoglobin (HbO2), and water ($H_2O$). In general, it was assumed that $\epsilon_{Mb} = \epsilon_{Hb}$ and $\epsilon_{MbO2} = \epsilon_{HbO2}$.

Using simulated spectra derived from Kienle's two-layer model, with the absorbance coefficient of the background $\mu_{a,back}(\lambda)$ corresponding to the absorbance coefficient of the system $\mu_{a,sys}(\lambda)$, it was observed that for simulated spectra corresponding to fat layers of thickness greater than 5 mm, scattering was dominated by the fat scattering component, such that scattering due to blood components was very small. However, experimentally measured spectra revealed a signal component that was relatively easy to attribute to scattering by blood components, implying that the functional form of the absorbance coefficient in Equation (23) may not always be correct. It is known, for example, that the volume fraction of the absorbing component in muscle tissue is approximately 2.2% (see, for example, Doornbos, et al, Phys. Med. Biol. 44, 967-981 (1999)), which corresponds to the volume of blood in the muscle tissue. Accordingly, to simulate spectra for prediction of HbT, the absorbance coefficient was assumed to take the functional form $$\mu_{a,sys}(\lambda) = 0.02 \cdot \mu_{a,tube}(\lambda) \tag{26}$$

The reduced scattering coefficient, $\mu_{s,sys}'(\lambda, Hct)$, can be expressed as follows:

$$\mu_{s,sys}'(\lambda, Hct) = (1-f)\mu_{s,back}'(\lambda) + f\mu_{s,tube}'(\lambda, Hct) \tag{27}$$

where the reduced scattering coefficient of the tube component, $\mu_{s,tube}'(\lambda, Hct)$, can be expressed as $$\mu_{s,tube}'(\lambda, Hct) = -0.00158(\lambda - 633) + 0.399 Hct + 1.926 \tag{28}$$

with Hct expressed as a volume percentage. Equation (28) was derived from Roggan et al., J. Biomed. Opt. 4: 36-46 (1999), the entire contents of which are incorporated by reference herein. The reduced scattering coefficient of the background component, $\mu_{s,back}'(\lambda)$, can be determined according to $$\mu_{s,back}'(\lambda) = a\lambda \times 10^{-3} + b \tag{29}$$

where a and b are adjustable parameters.

The quantities $c_{H2O}$ and Hct are related according to $$100 c_{H2O} + Hct = 100 \tag{30}$$

Further, the concentration of total hemoglobin, [HbT], is the sum of $c_{Hb}$ and $c_{HbO2}$, and Hct (%) = 3·[HbT], where [HbT] is in units of g/dl.

Using Equations (23)-(30), spectra were simulated using Farrell's one-layer and Kienle's two-layer models. Parameters used to generate the spectra were as follows:

20 HbT points in a range of concentrations from 0.15-3.0 mM (1.0-20 g/dl) tissue oxygen saturation $SO_2 = 0\%$, 25%, 50%, 75%, 100%
f = 0.01, 0.03, 0.05
a = −0.005, −0.001, −0.0005, −0.00005
b = −1, 0, 1, 2, 3

In addition, spectra for which the following conditions were observed were filtered out of the set of simulated spectra:

$C_{H2O} > 0.9$
$\mu_{s,back}'(\lambda) < 0$
$\mu_{s,tube}'(\lambda, Hct) < 0$
$\mu_{s,sys}(\lambda, Hct) < 1$
absorbance < 0 or absorbance is a complex number Using the above conditions and parameters, a total of 1885 spectra were simulated using Farrell's model (fat thickness = 0 mm), and a total of 2165 spectra were simulated for each fat thickness greater than zero using Kienle's model (fat thickness = 1 mm, 2 mm, 3 mm, 4 mm, 5 mm, 6 mm, 7 mm, and 8 mm). Accordingly, a total of 19205 spectra were simulated.

A subset of about 20% of the simulated spectra was randomly selected to serve as the test set. The remaining 80% of the simulated spectra were used to train a PLS model. Table 3 shows the number of spectra selected for the test set and the training set for each fat thickness.

TABLE 3

| | Fat Thickness | | | | | | | | |
|---|---|---|---|---|---|---|---|---|---|
| | 0 mm | 1 mm | 2 mm | 3 mm | 4 mm | 5 mm | 6 mm | 7 mm | 8 mm |
| Test Set | 336 | 400 | 390 | 389 | 391 | 391 | 392 | 386 | 386 |
| Training Set | 1549 | 1765 | 1775 | 1776 | 1774 | 1774 | 1773 | 1779 | 1779 |
| Total | 1885 | 2165 | 2165 | 2165 | 2165 | 2165 | 2165 | 2165 | 2165 |

The PLS model was trained as follows. First, the magnitudes of all simulated spectra (both in the test and training sets) were normalized by dividing each spectral value in the wavelength range from 735 nm to 880 nm by the mean magnitude of the spectrum. Second, PCA loading corrections were performed on spectra in both the training set and the test set. The loading vectors were selected from the training set, and the smallest value of HbT was selected as the analyte of interest.

Next, a PLS model for prediction of HbT was constructed from the PCA loading-corrected training spectra. For the training set of spectra (row 3 in Table 3), with 2 PCA loadings, the smallest HbT was used to train the PLS model with 22 PLS factors. Finally, the PLS model was applied to predict HbT values based on the PCA corrected test spectra (row 2 in Table 3) for each of the "samples" with different fat thicknesses. Since the actual values of HbT for each of the samples was known (as these values were used as input to the simulations, as discussed above), the predicted and actual values of HbT were compared. Correlation coefficients $R^2$, root mean-square errors of prediction (RMSEP), and error percent, which is the percentage ratio of RMSEP to the HbT range, which is 2.85(mM), were determined for each of the fat thicknesses. The results of these determinations are shown in Table 4.

TABLE 4

| | Fat Thickness (mm) | | | | | | | | |
|---|---|---|---|---|---|---|---|---|---|
| | 0 | 1 | 2 | 3 | 4 | 5 | 6 | 7 | 8 |
| $R^2$ | 0.972 | 0.979 | 0.980 | 0.978 | 0.979 | 0.976 | 0.979 | 0.974 | 0.958 |
| RMSEP | 0.123 | 0.111 | 0.106 | 0.114 | 0.117 | 0.119 | 0.112 | 0.118 | 0.153 |
| Error Percent (%) | 4.316 | 3.895 | 3.719 | 4.000 | 4.105 | 4.175 | 3.930 | 4.140 | 5.368 |

The results in Table 4 show that for fat thicknesses of between 1 mm and 7 mm, the estimated predictive error is less than 5%. This indicates that the methods and systems disclosed herein are capable of predicting hemoglobin concentrations over a wide range of variability in patient-specific parameters and conditions that influence light absorbance and scattering.

Other Embodiments

It is to be understood that the foregoing description is intended to illustrate and not limit the scope of the disclosure, which is defined by the scope of the appended claims. Other aspects, advantages, and modifications are within the scope of the following claims.

What is claimed is:

1. A system for determining a value associated with an analyte in a sample, the system comprising:
 a radiation source configured to direct radiation to be incident on the sample;
 a detector configured to detect radiation from the sample; and
 an electronic processor configured to:
  obtain measured spectral information about the sample based on the detected radiation;
  compare the measured spectral information to a set of reference spectra determined from a model for light attenuation in the sample to identify a member of the set of reference spectra that corresponds to the measured spectral information;
  correct the identified member of the set of reference spectra using a set of spectral correction factors determined from the set of reference spectra;
  select a subset of the reference spectra and use only the selected subset of the reference spectra to determine values of parameters associated with a calibration equation; and
  use the corrected identified member of the set of reference spectra as input to a calibration equation to determine the value associated with the analyte,
 wherein the electronic processor is further configured to select the subset of the reference spectra by:
  determining, for each of multiple subsets of the reference spectra, a set of values of the parameters associated with the calibration equation;
  determining a value of an error term associated with each set of values of the parameters; and
  selecting the subset of the reference spectra that produces the set of values of the parameters having the smallest error term.

2. The system of claim 1, wherein the electronic processor is configured to determine values associated with two or more analytes, and wherein the two or more analytes are selected from the group consisting of pH, temperature, oxygen tension, oxygen saturation, carbon dioxide partial pressure, hemoglobin concentration, water concentration, and hematocrit.

3. The system of claim 1, wherein the model comprises contributions from at least two different sources of light attenuation in the sample, and wherein the at least two different sources of light attenuation comprise light scattering and absorption.

4. The system of claim 3, wherein the light scattering comprises contributions from light scattering by one or more fat layers and light scattering by muscle tissue in the sample.

5. The system of claim 3, wherein the absorption comprises contributions from light absorption by at least two different analytes in the sample.

6. The system of claim 1, wherein the electronic processor is configured to determine the set of spectral correction factors by calculating mean-centered spectra from the set of reference spectra.

7. The system of claim 6, wherein the electronic processor is configured to determine the set of spectral correction factors by calculating orthogonalized spectra based on the mean-centered spectra.

8. The system of claim 1, wherein the electronic processor is configured to identify a member of the set of reference spectra that corresponds to the measured spectral information by determining a member of the set of reference spectra that matches most closely with the measured spectral information.

9. The system of claim 8, wherein the electronic processor is configured to determine the member of the set of reference spectra that matches most closely with the measured spectral information based on maximum and minimum differences between the measured spectral information and at least some members of the set of reference spectra.

10. The system of claim 1, wherein the electronic processor is configured to select the subset of the set of reference spectra based on the analyte.

11. A system for determining a value associated with an analyte in a sample, the system comprising:
 a radiation source configured to direct radiation to be incident on the sample;
 a detector configured to detect radiation from the sample; and
 an electronic processor configured to:
  determine values of a set of parameters associated with a calibration equation for calculating the value of the analyte based on a set of reference spectra determined from a model for light attenuation in the sample and not on measured spectral information;
  identify a member of the set of reference spectra that most closely corresponds to measured spectral information for the sample; and
  determine the value associated with the analyte by using the identified member as input to the calibration equation,
 wherein the electronic processor is configured to determine the values of the set of parameters by:
  determining, for each of multiple subsets of the reference spectra, a set of values of the parameters associated with the calibration equation;
  determining a value of an error term associated with each set of values of the parameters; and
  using the set of values of the parameters having the smallest associated error term to determine the value associated with the analyte.

12. The system of claim 11, wherein the model for light attenuation comprises contributions from light scattering and from light absorption by at least two different analytes in the sample, and wherein the two different analytes comprise at least one of oxygenated hemoglobin, de-oxygenated hemoglobin, and myoglobin.

13. The system of claim 11, wherein the analyte comprises at least one member selected from the group consisting of pH, temperature, oxygen tension, oxygen saturation, carbon dioxide partial pressure, hemoglobin concentration, water concentration, and hematocrit.

14. The system of claim 11, wherein the electronic processor is configured to determine the value associated with the analyte by:
 determining spectral correction factors associated with the analyte from the set of reference spectra;
 applying the spectral correction factors to the identified member of the set of reference spectra to correct the identified member; and
 using the corrected identified member as input to the calibration equation.

15. The system of claim 11, wherein the model comprises contributions from at least two different sources of light attenuation in the sample, and wherein the at least two different sources of light attenuation comprise light scattering and absorption.

16. The system of claim 11, wherein the electronic processor is configured to select a subset of the set of reference spectra to determine the values of the set of parameters associated with the calibration equation and to select the subset based on the analyte.

* * * * *